United States Patent
Komori

(10) Patent No.: US 8,734,690 B2
(45) Date of Patent: May 27, 2014

(54) PRODUCTION METHOD OF ORTHODONTIC BRACKET WITH POSITIONING GUIDE

(75) Inventor: Akira Komori, Meguro-ku (JP)

(73) Assignee: GC Corporation, Tokyo (JP)

( * ) Notice: Subject to any disclaimer, the term of this patent is extended or adjusted under 35 U.S.C. 154(b) by 568 days.

(21) Appl. No.: 12/791,497

(22) Filed: Jun. 1, 2010

(65) Prior Publication Data

US 2010/0300615 A1 Dec. 2, 2010

(30) Foreign Application Priority Data

Jun. 1, 2009 (JP) ................................. 2009-132466

(51) Int. Cl.
 *B29C 35/02* (2006.01)
(52) U.S. Cl.
 USPC ........................................................ 264/16
(58) Field of Classification Search
 USPC .......................................................... 264/16
 See application file for complete search history.

(56) References Cited

U.S. PATENT DOCUMENTS

| | | | |
|---|---|---|---|
| 4,892,478 A * | 1/1990 | Tateosian et al. ................. | 433/6 |
| 6,174,163 B1 | 1/2001 | Hiro | |
| 2005/0136370 A1 | 6/2005 | Brennan et al. | |
| 2008/0187878 A1 | 8/2008 | Brennan et al. | |

FOREIGN PATENT DOCUMENTS

| | | |
|---|---|---|
| EP | 0 941 710 | 9/1999 |
| JP | 11-99161 | 4/1999 |
| WO | WO 2005/065568 | 7/2005 |

OTHER PUBLICATIONS

Search Report issued Sep. 20, 2010, in European patent application No. 10005704.1.

* cited by examiner

*Primary Examiner* — Ryan Ochylski
(74) *Attorney, Agent, or Firm* — Oblon, Spivak, McClelland, Maier & Neustadt, L.L.P.

(57) ABSTRACT

An orthodontic bracket with a positioning guide is produced by thinly coating a first dental photopolymerizable composition 1 on a bonding surface of each orthodontic bracket B, building a second dental photopolymerizable composition 2 adhesive to the first composition 1 on the bonding surface, adhering it to a tooth surface of a dentition gypsum model 3 reproducing a patient's dentition, a separating material being previously coated on the tooth surface of the gypsum model 3, polymerizing/curing the first and second compositions 1 and 2 by irradiating light, thinly coating a third dental photopolymerizable composition 4 on a tongue side and/or a cheek side entire surface around the orthodontic bracket B on the gypsum model 3, the third composition 4 being easily abraded when an occlusal pressure is acted, and polymerizing/curing the third composition 4 by irradiating light to be integrated with at least the second composition 2.

12 Claims, 3 Drawing Sheets

PRODUCTION METHOD OF ORTHODONTIC BRACKET WITH POSITIONING GUIDE

BACKGROUND OF THE INVENTION

1. Field of the Invention

The present invention relates to a production method of an orthodontic bracket with a positioning guide, which is bonded and fixed on a tongue side surface and/or a cheek side surface of each tooth of a patient.

2. Description of the Conventional Art

In an orthodontic treatment, since a movement of a tooth changes greatly with a slight difference of an installing position of an orthodontic bracket, it is very important to install the orthodontic bracket at a proper position.

In order to more accurately determine an installing position of an orthodontic bracket, a method called an indirect method or an indirect bonding method has been performed. In the indirect bonding method, a dental technician predetermines the installing position of an orthodontic bracket on a dentition gypsum model reproducing a dentition of a patient, adjusts the installing position so as to accurately install the orthodontic bracket to a tooth of the patient, and then, the dental technician installs the orthodontic bracket to the tooth of the patient. However, even though the installing position is predetermined on the dentition gypsum model as mentioned above, the orthodontic bracket easily deviates from the proper position when the dental technician actually installs the orthodontic bracket to the tooth of the patient. Thus, it is difficult to reproduce the accurate installing position.

For example, Japanese Patent Application Laid-Open No. 11-99161 discloses a method to solve the aforementioned problem. This method includes the steps of positioning an orthodontic bracket to each of teeth of a dentition gypsum model of a patient, supplying an uncured resin to each tooth of the dentition gypsum model, and forming independently for every tooth, a independent resin core for installing bracket, in which an advance part and a core part are integrally formed, the advance part is filled between a tooth and a base of the bracket positioned at the tooth, and the core part extends from the advance part to a cut edge or an occlusal surface of the tooth. The method further includes the steps of taking-out the independent resin core for installing bracket, which is integrated with the bracket, from each tooth of the dentition gypsum model, installing and bonding the taken-out independent resin core for installing bracket to each corresponding tooth of the patient, and removing each of the independent resin core parts for installing the bracket.

According to this installing method, since the core part independently formed at each tooth has a shape matching the cut edge or occlusal surface of each tooth of the patient, the bracket can be installed to a proper position by only fitting the core part to each tooth of the patient so as to cover the tooth. However, in this method, since a thickness of the core part is thick in a degree similar to that of the advance part, each disused core part should be removed after having installed the bracket to each tooth to be treated of the patient. Thus, the method needs much time and work, and has a problem that the installing position easily deviates when removing the disused core parts. Further, if the core parts are not completely removed, a residual resin could damage the cut edges or the occlusal surfaces of teeth clenched at a time of occlusion. Furthermore, since a normal temperature polymerizing resin is used for forming the advance part and the core part, an operation time is limited. Thus, it is hard to form the independent resin core having a shape fitting to each tooth to be treated of the patient.

SUMMARY OF THE INVENTION

Problem to be Solved by the Invention

Taking into consideration the problem mentioned above, the present invention is directed to a production method of an orthodontic bracket with a positioning guide, according to which an orthodontic bracket can be easily installed at an accurate position, it is not necessary to remove a resin and the like after having installed the orthodontic bracket, a residual resin and the like do not damage a cut edge or an occlusal surface of a tooth, and the orthodontic bracket can be produced with an enough operation time.

Means for Solving the Problem

Present inventors carried out earnest works to solve the aforementioned problems, and as a result, they found out that an orthodontic bracket with a positioning guide, which is bonded and fixed on a tongue side surface and/or a cheek side surface of each tooth of a patient, is produced as follows, to complete the present invention. A first dental photopolymerizable composition as a base material is thinly coated on a bonding surface of each orthodontic bracket mounted to an orthodontic wire, where the bonding surface is to be bonded to a tooth surface. In order to fill a gap which occurs between the tooth surface and the bonding surface of the orthodontic bracket at a time of bonding the orthodontic bracket to a tooth of a patient, a second dental photopolymerizable composition having an adhesive property to the first dental photopolymerizable composition is built on the bonding surface of the orthodontic bracket. The bonding surface is adhered to a tooth surface of a dentition gypsum model reproducing a dentition of the patient, where a separating material is previously coated on the tooth surface of the dentition gypsum model and the first dental photopolymerizable composition and the second dental photopolymerizable composition are polymerized/cured by irradiating light. Then, a third dental photopolymerizable composition, which is easily abraded when an occlusal pressure is acted, is thinly coated on a tongue side entire surface and/or a cheek side entire surface around the orthodontic bracket on the dentition gypsum model, and is polymerized/cured so as to be integrated with at least the second dental photopolymerizable composition by irradiating light. By performing these processes, the orthodontic bracket with a positioning guide, which is bonded and fixed on a tongue side surface and/or a cheek side surface of each tooth of a patient can be produced. According to this orthodontic bracket with a positioning guide, since the second dental photopolymerizable composition is built and cured between the tooth surface on the dentition gypsum model and the bonding surface of the orthodontic bracket on which the base material is previously coated, the orthodontic bracket can be stably installed by forming a surface fitting to ups and downs of the tooth surface, and on the tooth surface. In addition, since the third dental photopolymerizable composition is thinly coated and cured on the tongue side entire surface and/or the cheek side entire surface around the orthodontic bracket on the dentition gypsum model, a shape of the tooth surface at which the orthodontic bracket is positioned is transferred with the second dental photopolymerizable composition, and a shape of the tooth surface of a part at which the orthodontic bracket is not positioned is transferred with the third dental photopolymerizable composition, so as to become a positioning guide part to which shapes of the tongue side entire surface and/or the cheek side entire surface are transferred. By installing the orthodontic bracket to the actual tooth surface in a manner that the guide part is fitted, the orthodontic bracket can be steadily installed to an accurate position. Further, since there is no thick core part at a cut edge or an occlusal surface of a tooth, it is not necessary to spend time and work to remove disused parts. Particularly, the third dental photopolymerizable composition coated around the orthodontic bracket is composed by a material which is easily abraded when an occlusal pressure is acted. Thus, even when the third dental photopolymerizable composition is in contact with cut edges of clenched teeth at a time of occlusion, the third dental photopolymerizable composition does not damage the teeth. Further, even when occlusion becomes unsmooth by the third dental photopolymerizable composition, the third dental photopolymerizable composition is easily abraded and removed naturally. Furthermore, the first, second, and third dental photopolymerizable compositions used in this method are photopolymerizable compositions, and are not polymerized/cured unless irradiating light. Thus, the orthodontic bracket with a positioning guide can be produced with an enough operation time.

That is, the present invention is a production method of an orthodontic bracket with a positioning guide, which is bonded and fixed on a tongue side surface and/or a cheek side surface of each tooth of a patient, the production method including processes of thinly coating a first dental photopolymerizable composition as a base material on a bonding surface of each orthodontic bracket mounted to an orthodontic wire, where the bonding surface is to be bonded to a tooth surface, building a second dental photopolymerizable composition having an adhesive property to the first dental photopolymerizable composition on the bonding surface of the orthodontic bracket, in order to fill a gap which occurs between the tooth surface and the bonding surface of the orthodontic bracket at a time of bonding the orthodontic bracket to a tooth of a patient, adhering the bonding surface to a tooth surface of a dentition gypsum model reproducing a dentition of the patient, where a separating material is previously coated on the tooth surface of the dentition gypsum model, polymerizing/curing the first dental photopolymerizable composition and the second dental photopolymerizable composition by irradiating light, then thinly coating a third dental photopolymerizable composition, which is easily abraded when an occlusal pressure is acted, on a tongue side entire surface and/or a cheek side entire surface around the orthodontic bracket on the dentition gypsum model, and polymerizing/curing the third dental photopolymerizable composition by irradiating light so as to be integrated with at least the second dental photopolymerizable composition.

When the dentition gypsum model reproducing a dentition of a patient is a dentition gypsum model produced based on an impression taken from the patient, the dentition gypsum model can be accurately and easily produced, so it is preferable. Further, when the dentition gypsum model is a dentition gypsum model in which each tooth is separated from the dentition gypsum model produced based on the taken impression, moved to a position at which the tooth should be placed after orthodontic treatment, and fixed at the position, the installing position of the orthodontic bracket can be accurately determined based on the position at which the tooth should be finally placed after the orthodontic treatment, so it is preferable.

EFFECT OF THE INVENTION

A production method of an orthodontic bracket with a positioning guide according to the present invention is to produce an orthodontic bracket with a positioning guide which is bonded and fixed on a tongue side surface and/or a cheek side surface of each tooth of a patient, the production method including the processes of thinly coating a first dental photopolymerizable composition as a base material on a bonding surface of each orthodontic bracket mounted to an orthodontic wire, where the bonding surface is to be bonded to a tooth surface, building a second dental photopolymerizable composition having an adhesive property to the first dental photopolymerizable composition on the bonding surface of the orthodontic bracket in order to fill a gap which occurs between the tooth surface and the bonding surface of the orthodontic bracket at a time of bonding the orthodontic bracket to a tooth of a patient, adhering the bonding surface to a tooth surface of a dentition gypsum model reproducing a dentition of the patient, where a separating material is previously coated on the tooth surface of the dentition gypsum model, and polymerizing/curing the first dental photopolymerizable composition and the second dental photopolymerizable composition by irradiating light, then, thinly coating a third dental photopolymerizable composition, which is easily abraded when an occlusal pressure is acted, on a tongue side entire surface and/or a cheek side entire surface around the orthodontic bracket on the dentition gypsum model, and is polymerizing/curing the third dental photopolymerizable composition by irradiating light so as to be integrated with at least the second dental photopolymerizable composition. According to this orthodontic bracket with a positioning guide produced, since the second dental photopolymerizable composition is built and cured between the tooth surface on the dentition gypsum model and the bonding surface of the orthodontic bracket on which the base material is previously coated, the orthodontic bracket can be stably installed by forming a surface fitting to ups and downs of the tooth surface on the tooth surface. In addition, since the third dental photopolymerizable composition is thinly coated and cured on the tongue side entire surface and/or the cheek side entire surface around the orthodontic bracket on the dentition gypsum model, a shape of a part of the tooth surface at which the orthodontic bracket is positioned is transferred with the second dental photopolymerizable composition, and a shape of the tooth surface of a part at which the orthodontic bracket is not positioned is transferred with the third dental photopolymerizable composition, so as to become a positioning guide part to which shapes of the tongue side entire surface and/or the cheek side entire surface are transferred. By installing the orthodontic bracket to the actual tooth surface in a manner that the guide part is fitted, the orthodontic bracket can be steadily installed to an accurate position. Further, since there is no thick core part at a cut edge or an occlusal surface of a tooth, it is not necessary to spend time and work to remove disused portions. Particularly, the third dental photopolymerizable composition coated around the orthodontic bracket is composed by a material which is easily abraded when an occlusal pressure is acted. Thus, even when the third dental photopolymerizable composition is in contact with cut edges of clenched teeth at a time of occlusion, the third dental photopolymerizable composition does not damage the teeth. Further, even when occlusion becomes unsmooth by the third dental photopolymerizable composition, the third dental photopolymerizable composition is easily abraded and is removed naturally. Furthermore, the first, second, and third dental photopolymerizable compositions used in the production method of the orthodontic bracket with a positioning guide according to the present invention are photopolymerizable compositions, and are not polymerized/cured unless irradiating light. Thus, the orthodontic bracket with a positioning guide can be produced with an enough operation time.

Further, when a dentition gypsum model reproducing a dentition of a patient is a dentition gypsum model produced based on an impression taken from the patient, the dentition gypsum model can be accurately and easily produced, so it is preferable. Further, when the dentition gypsum model is a dentition gypsum model in which each tooth is separated from the dentition gypsum model produced based on the taken impression, moved to a position at which the tooth should be placed after orthodontic treatment, and fixed at the position, the installing position of the orthodontic bracket can be accurately determined based on the position at which the tooth should be finally placed after the orthodontic treatment, so it is preferable.

DETAILED DESCRIPTION OF PREFERRED EMBODIMENT

Figure 1:
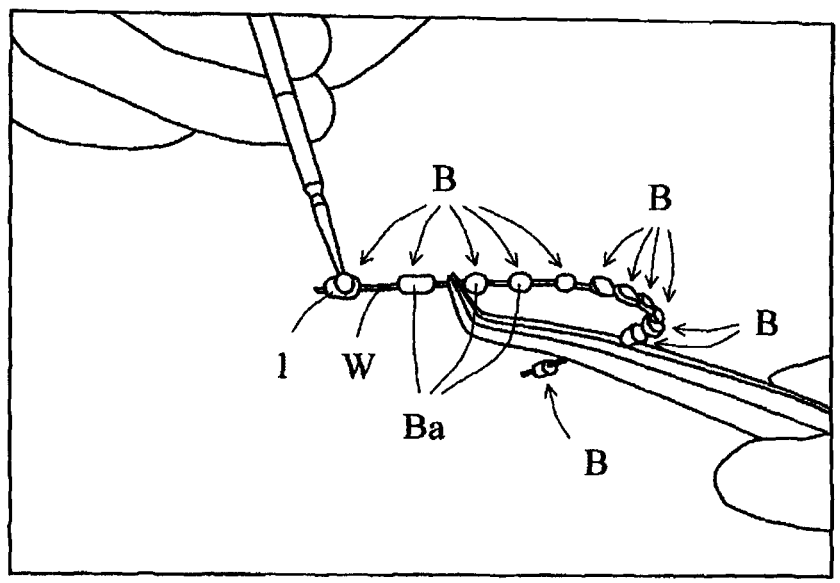
FIG. 1 is a perspective view illustrating a state that a first dental photopolymerizable composition as a base material is thinly coated on a bonding surface of an orthodontic bracket mounted to an orthodontic wire, where the bonding surface is to be bonded to a tooth surface.

A production method of an orthodontic bracket with a positioning guide according to the present invention will be described in detail below with reference to the drawings.

In the drawings, an orthodontic wire W, an orthodontic bracket B mounted to the orthodontic wire W, and an orthodontic bracket with a poisoning guide GB are illustrated.

A first dental photopolymerizable composition 1 as a base material is thinly coated on a bonding surface Ba of each of the orthodontic brackets B mounted to the orthodontic wire W, where the bonding surface Ba is to be bonded to a tooth surface. The first dental photopolymerizable composition 1 could be a composition which mainly includes a (meth)acrylate compound and inorganic filler and also includes a small amount of a photopolymerization catalyst. Particularly, a composition having a low viscosity is preferably used since the composition is thinly coated as a base material.

A second dental photopolymerizable composition 2 has an adhesive property to the first dental photopolymerizable composition 1. The second dental photopolymerizable composition 2 is built on the bonding surface Ba of the orthodontic bracket B in order to fill a gap between a tooth surface and the bonding surface Ba of the orthodontic bracket B, where the gap occurs when the orthodontic bracket B is bonded to a tooth of a patient. The second dental photopolymerizable composition 2 can also mainly include a (meth)acrylate compound and inorganic filler, and include a small amount of a photopolymerization catalyst. However, since the second dental photopolymerizable composition 2 should be built on the bonding surface Ba of the orthodontic bracket B in order to fill the gap between the tooth surface and the bonding surface Ba of the orthodontic bracket B, the second dental photopolymerizable composition 2 having high viscosity is preferably used.

A dentition gypsum model 3 reproduces a dentition of a patient. As for such a dentition gypsum model, when the dentition gypsum model reproducing a dentition of a patient is a dentition gypsum model produced based on an impression taken from the patient, the dentition gypsum model can be accurately and easily produced, so it is preferable. Further, when the dentition gypsum model is a dentition gypsum model in which each tooth is separated from the dentition gypsum model produced based on the taken impression, moved to a position at which the tooth should be placed after orthodontic treatment, and fixed at the position, the installing position of the orthodontic bracket can be accurately determined based on the position at which the tooth should be finally placed after the orthodontic treatment, so it is preferable.

A third dental photopolymerizable composition 4 is thinly coated on a tongue side entire surface and/or a cheek side entire surface around the orthodontic bracket B on the dentition gypsum model 3. The third dental photopolymerizable composition 4 is obtained by adding an organic filler to a (meth)acrylate compound so as to be easily abraded when an occlusal pressure is acted. However, preferably, the third dental photopolymerizable composition 4 can include an inorganic filler in such an amount as to obtain sufficient strength and rigidity, when the strength and rigidity is insufficient, and include a small amount of a photopolymerization catalyst.

The (meth)acrylate compound included in the first dental photopolymerizable composition 1, the second dental photopolymerizable composition 2, and the third dental photopolymerizable composition 4 according to the present invention means various kinds of acrylate or methacrylate monomers, oligomers, and prepolymers.

More particularly, the (meth)acrylate compound could be methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-ethylhexyl (meth)acrylate, benzyl (meth)acrylate, 2-hydroxy-1,3-di(meth)acryloxy propane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylolethane tri(meth)acrylate, pentaerythritol tetra(meth)acrylate, polybutylene glycol di(meth)acrylate, or bisphenol A diglycidyl (meth)acrylate. A monomer, oligomer, and prepolymer of these compounds can be preferably used. Further, as for (meth)acrylate having urethane bond, di-2-(meth)acryloxyethyl-2,2,4-trimethylhexamethylene dicarbamate, 1,3,5-tris [1,3-bis{(meth)acryloyloxy}-2-propoxycarbonylaminohexane]-1,3,5-(1H,3H,5H) triazine-2,4,6-trione, and 2,2-bis-4-(3-(meth)acryloyloxy-2-hydroxypropyl)-phenylpropane, can be used. In addition, (meth)acrylate of urethane oligomer including 2,2'-di(4-hydroxycyclohexyl) propane, 2-oxypanone, hexamethylene diisocyanate, and 2-hydroxyethyl (meth)acrylate, and (meth)acrylate of urethane oligomer including 1,3-butanediol, hexamethylene diisocyanate, and 2-hydroxyethyl (meth)acrylate can be used. These (can be used independently or by mixing two or more kinds.

The inorganic filler included in the first dental photopolymerizable composition 1, the second dental photopolymerizable composition 2 and the third dental photopolymerizable composition 4 could be powders of as anhydrous silicic acid, glasses, such as barium glass, strontium glass, alumina glass, potassium glass, fluorcaluminosilicate glass, and the like, synthetic zeolite, calcium phosphate, feldspar, fumed silica, aluminum silicate, calcium silicate, magnesium carbonate, alumina, zirconia, magnesia, titania, hydrous silicic acid, hydrous calcium silicate, hydrous aluminum silicate, quartz, or the like. In addition, a non-porous colloidal silica by the atomized method, a non-porous colloidal alumina, non-porous colloidal titania, or a non-porous colloidal silica by the wetting method can be used.

The organic filler included in the third dental photopolymerizable composition 4 could be a methacrylate, acrylate, or styrene homopolymer including a bridging agent, or its copolymer. More particularly, the organic filler could be trimethylolpropane trimethylmethacrylate or its acrylate, or a homopolymer bridged with other bridging agents or the like or its copolymer.

In order to bond with (meth)acrylate, the filler can be subjected to a surface treatment with a silane coupling agent, such as γ-methacryloxypropyltrimethoxysilane, vinyltrichlorosilane, vinyltriethoxysilane, vinyltrimethoxysilane, vinyltriacetoxysilane, vinyltri(methoxyethoxy) silane, or the like.

In general, the photopolymerization catalyst included in the first dental photopolymerizable composition 1, the second dental photopolymerizable composition 2, and the third dental photopolymerizable composition 4 could be a combination of an initiator and a reducing agent. The initiator could be camphorquinone, benzyl, diacetyl, benzyl dimethyl ketal, benzyl diethyl ketal, benzyl di(2-methoxyethyl) ketal, 4,4'-dimethylbenzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluorothioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl) ketone, 4,4'-bisdiethylaminobenzophenone, a derivative of acylphosphine oxide, and a compound including an azide group, or the like. These are used independently or by mixing two or more kinds. Generally, as the reducing agent, tertamine or the like is used. Preferably, the tert-amine could be N,N-dimethyl-p-toluidine, N,N-dimethylaminoethylmethacrylate, triethanol amine, 4-dimethylamino benzoic acid methyl, 4-dimethylamino benzoic acid ethyl, or 4-dimethylamino benzoic acid isoamyl. As for other reducing agents, a benzoyl peroxide, a sodium sulfinate derivative, an organic metallic compound, or the like can be used.

A production method of the orthodontic bracket with a positioning guide GB according to the present invention will be described. The dentition gypsum model 3 reproducing a dentition of a patient is firstly produced. When the dentition gypsum model 3 is produced based on an impression previously taken from the patient, a dentition of the patient can be accurately and easily reproduced. A dentition of the dentition gypsum model 3 is the same as the current dentition of the patient. Thus, based on the dentition gypsum model 3, the position of the orthodontic bracket B can be determined very accurately. Further, the orthodontic bracket with a positioning guide GB produced by the production method according to the present invention has a positioning guide and accurately reproduces the position determined in the dentition gypsum model 3 on a real tooth of the patient.

The dentition gypsum model 3 produced based on the impression taken from the patient represents a dentition state before an orthodontic treatment. Thus, in an actual treatment, a dentist should adjust an orthodontic wire and the like so as to apply proper force to each tooth before the orthodontic treatment, while imaging the dentition state after the orthodontic treatment. Therefore, this adjustment is very hard.

Hence, the dentition gypsum model 3 in which each tooth is once separated from the dentition gypsum model 3 after the dentition gypsum model 3 is produced based on the impression taken from the patient, and moved to the position at which the tooth should be placed after the orthodontic treatment, can be used.

In this case, after determining the position of the orthodontic bracket B in this dentition gypsum model 3 having an ideal dentition state, the orthodontic bracket B is installed to the tooth of the patient before the actual orthodontic treatment. Therefore, the installing position of the orthodontic bracket B becomes ideal. The dentition gypsum model 3 having such the ideal dentition state can be used because the orthodontic bracket with a positioning guide GB produced by the production method according to the present invention has a positioning guide and can accurately reproduce the position determined in the dentition gypsum model 3 on the real tooth of the patient.

In order to produce the orthodontic bracket with a positioning guide GB by using such the dentition gypsum model 3, each orthodontic bracket B previously mounted to the orthodontic wire W is prepared first. Then, as illustrated in FIG. 1, the first dental photopolymerizable composition 1 as a base material is thinly coated on the bonding surface Ba of the orthodontic bracket B.

Figure 2:
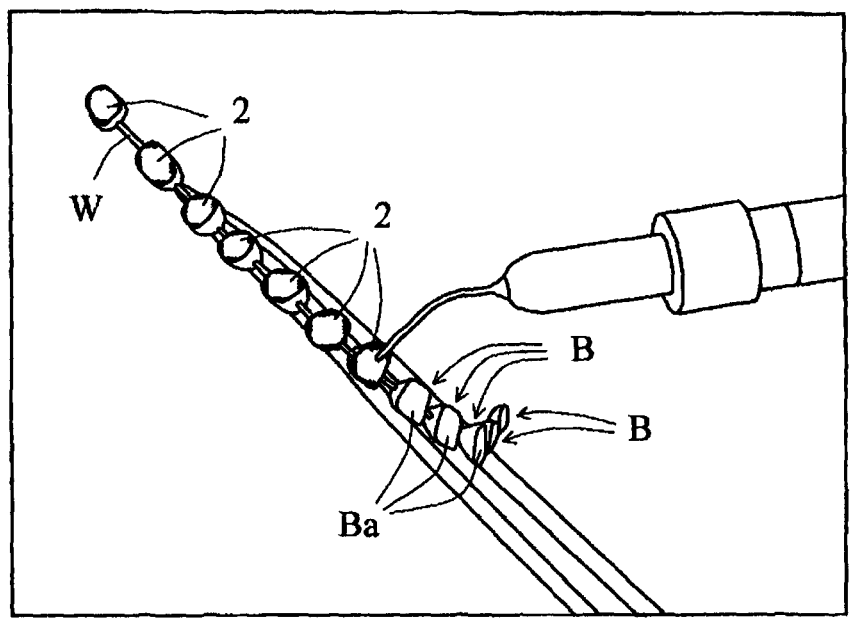
FIG. 2 is a perspective view illustrating a state that a second dental photopolymerizable composition is built after the first dental photopolymerizable composition has been coated.

In the state that the first dental photopolymerizable composition 1 is coated to form a primer layer for the second dental photopolymerizable composition 2 on the bonding surface Ba of the orthodontic bracket B, the second dental photopolymerizable composition 2 having an adhesive property to the first dental photopolymerizable composition 1 is built as illustrated in FIG. 2.

Figure 3:
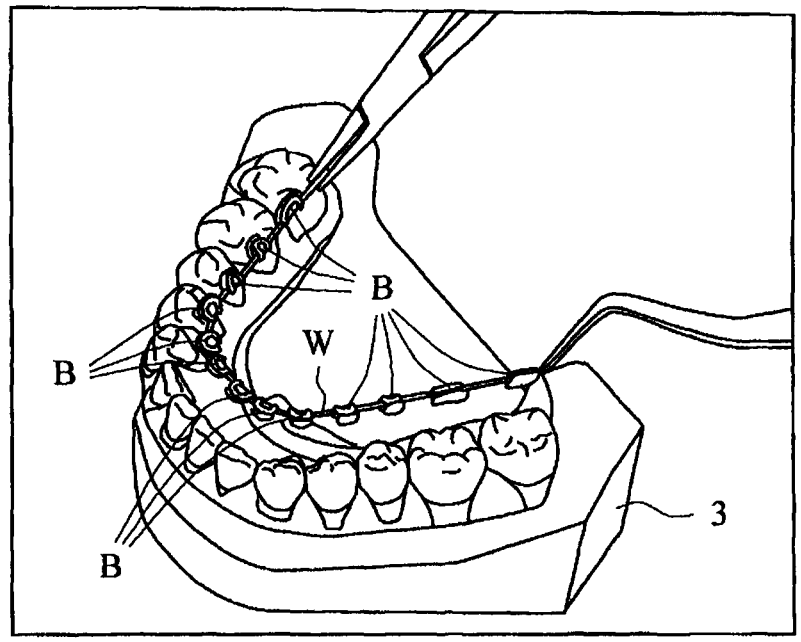
FIG. 3 is a perspective view illustrating a state that the orthodontic bracket illustrated in FIG. 2 is adhered to a tongue side surface of a tooth of a dentition gypsum model and is positioned, where the tooth is separated from the dentition gypsum model produced based on an impression taken from a patient, moved to a position at which the tooth should be placed after orthodontic treatment, and fixed at the position.
Figure 4:
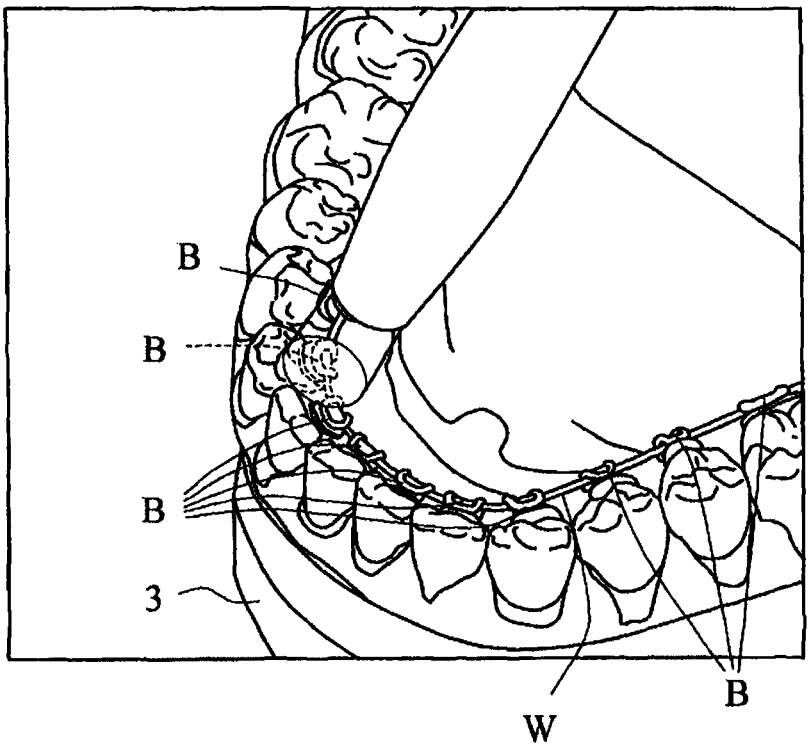
FIG. 4 is a perspective view illustrating a state that the orthodontic bracket illustrated in FIG. 3 is irradiated with light for polymerizing/curing.

In the state that the second dental photopolymerizable composition 2 is built on the bonding surface Ba of the orthodontic bracket B as mentioned above, the orthodontic bracket B is adhered, through the second dental photopolymerizable composition 2, to and temporarily fixed on a tongue side surface of a tooth, on which a separating material is previously coated on the dentition gypsum model 3, as illustrated in FIG. 3. Then, the first dental photopolymerizable composition 1 and the second dental photopolymerizable composition 2 are polymerized/cured by irradiating light to the orthodontic bracket B, the installing position of which has been determined, as illustrated in FIG. 4.

Figure 5:
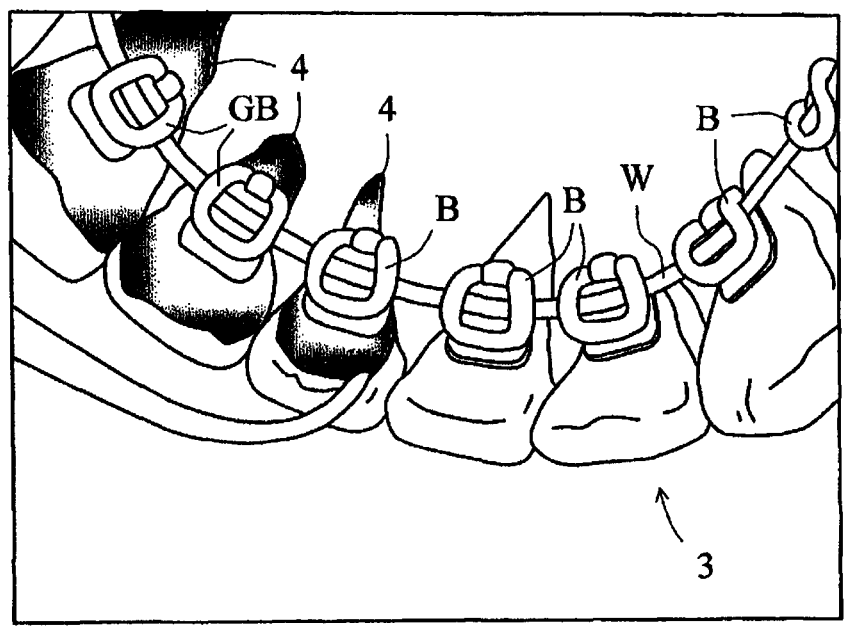
FIG. 5 is a perspective view illustrating a state that a third dental photopolymerizable composition is thinly coated on a tongue side entire surface around an or orthodontic bracket.

Next, as illustrated in FIG. 5, the third dental photopolymerizable composition 4 is thinly coated on the tongue side entire surface around the orthodontic bracket B on the dentition gypsum model 3. The third dental photopolymerizable composition 4 is then polymerized/cured by irradiating light so as to be integrated with at least the second dental photopolymerizable composition 2. Therefore, when the orthodontic bracket B is removed from the dentition gypsum model 3, the orthodontic bracket B can be removed in a state of integrally having the three dental photopolymerizable compositions as a whole.

Accordingly, a shape of a tongue side surface at which the orthodontic bracket B is positioned is transferred with the second dental photopolymerizable composition 2, and a shape of the tongue side surface of a part at which the orthodontic bracket B is not positioned is transferred with the third dental photopolymerizable composition 4. Since a shape of an entire surface of the tongue side surface is thus transferred to these photopolymerizable compositions, the orthodontic bracket with a positioning guide GB can be stably installed to an accurate installing position by coating a bonding agent to the positioning guide and installing it so as to fit the tongue side surface of a real tooth.

Further, the orthodontic bracket with a positioning guide GB to be installed to a cheek side surface of a tooth can be similarly produced by the production method according to the present invention. For example, when the orthodontic bracket with a positioning guide GB is installed to a front tooth, appearance of which is worried, the orthodontic bracket with a positioning guide GB can be installed to a tongue side surface of the front tooth. When the orthodontic bracket with a positioning guide GB is installed to a molar tooth, the orthodontic bracket with a positioning guide GB can be installed to a cheek side surface of the molar tooth, for which an installing operation or the like is easy. Further it can be installed only to a cheek side surface, for which an installing operation or the like is easy. Embodiments of these examples are not illustrated in the drawings.

In an orthodontic treatment, a combination of an orthodontic tube and an orthodontic pendulum can be used instead of the combination of the orthodontic bracket B and the orthodontic wire W, where the shapes and mounting states of these combinations are approximately similar. The orthodontic tube has a shape approximately similar to the shape of the orthodontic bracket B. The state of mounting the orthodontic tube to the orthodontic pendulum is approximately similar to the state of mounting the orthodontic bracket B to the orthodontic wire W. Therefore, the production method of the present invention can be applied to both the combinations without a difference at all. While the orthodontic tube is generally mounted on the tongue side surface of a tooth, the orthodontic tube to be mounted on the tongue side surface can also be easily produced by the production method according to the present invention.

What is claimed is:

1. A method for production of an orthodontic bracket with a positioning guide, which is bonded and fixed on a tongue side surface and/or a cheek side surface of each tooth of a patient, the method comprising:

coating a first dental photopolymerizable composition as a base material on a bonding surface of each orthodontic bracket mounted on an orthodontic wire, wherein the bonding surface of each orthodontic bracket is to be bonded to a surface of a corresponding tooth of a patient; then building a second dental photopolymerizable composition having an adhesive property to said first dental photopolymerizable composition, on the bonding surface of the orthodontic bracket, in order to fill a gap which occurs between the tooth surface and the bonding surface of the orthodontic bracket at a time of bonding the orthodontic bracket to a tooth of the patient; then adhering the bonding surface to a tooth surface of a dentition gypsum model reproducing a dentition of the patient, wherein a separating material is previously coated on the tooth surface of the dentition gypsum model; then polymerizing/curing said first dental photopolymerizable composition and said second dental photopolymerizable composition by irradiating light; then coating a third dental photopolymerizable composition, which is abraded when an occlusal pressure is acted on a tongue side entire surface and/or a cheek side entire surface around the orthodontic bracket on the dentition gypsum model; and then polymerizing/curing the third dental photopolymerizable composition by irradiating light, thereby integrating with at least the second dental photopolymerizable composition.

2. The method of claim 1, wherein the dentition gypsum model reproducing the dentition of the patient is a dentition gypsum model produced based on an impression taken from the patient, or wherein the dentition gypsum model is a dentition gypsum model in which each tooth is separated from the dentition gypsum model produced based on the impression taken from the patient, moved to a position at which the tooth should be placed after an orthodontic treatment, and fixed at the position.

3. The method of claim 1, wherein the first dental photopolymerizable composition comprises at least one (meth)acrylate compound, at least one inorganic filler, and at least one photopolymerization catalyst.

4. The method of claim 3, wherein the (meth)acrylate compound in the first dental photopolymerizable composition is at least one compound selected from the group consisting of an acrylate and/or methacrylate monomer, an oligomer thereof, and a prepolymer thereof.

5. The method of claim 3, wherein the (meth)acrylate compound in the second dental photopolymerizable composition is at least one compound selected from the group consisting of an acrylate and/or methacrylate monomer, an oligomer thereof, and a prepolymer thereof.

6. The method of claim 3, wherein the (meth)acrylate compound in the third dental photopolymerizable composition is at least one compound selected from the group consisting of an acrylate and/or methacrylate monomer, an oligomer thereof, and a prepolymer thereof.

7. The method of claim 1, wherein the second dental photopolymerizable composition comprises at least one (meth)acrylate compound, at least one inorganic filler, and at least one photopolymerization catalyst.

8. The method of claim 1, wherein the first, second, and/or third dental photopolymerizable composition comprises at least one (meth)acrylate compound, at least one inorganic filler, and at least one photopolymerization catalyst.

9. The method of claim 8, wherein the third dental photopolymerizable composition comprises at least one organic filler selected from the group consisting of a homopolymer of methacrylate, acrylate, and styrene, and at least one copolymer thereof.

10. The method of claim 8, wherein the third dental photopolymerizable composition comprises at least one organic filler selected from the group consisting of trimethylolpropane trimethylmethacrylate, its acrylate, its homopolymer bridged with at least one bridging agents, and its copolymer.

11. The method of claim 8, further comprising surface treating the at least one organic filler with at least one silane coupling agent selected from the group consisting of γ-methacryloxypropyltrimethoxysilane, vinyltrichlorosilane, vinyltriethoxysilane, vinyltrimethoxysilane, vinyltriacetoxysilane, and vinyltri (methoxyethoxy) silane.

12. The method of claim 1, wherein the first, second, and/or third dental photopolymerizable composition comprises at least one photopolymerization catalyst comprising at least one initiator and at least one reducing agent.

* * * * *